(12) United States Patent
Lyons et al.

(10) Patent No.: US 8,231,892 B2
(45) Date of Patent: Jul. 31, 2012

(54) BIODEGRADABLE DRUG DELIVERY SYSTEM

(75) Inventors: Robert T. Lyons, Laguna Hills, CA (US); James A. Burke, Santa Ana, CA (US); Michael R. Robinson, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 531 days.

(21) Appl. No.: 11/753,419

(22) Filed: May 24, 2007

(65) Prior Publication Data

US 2008/0292679 A1 Nov. 27, 2008

(51) Int. Cl.
*A61F 2/14* (2006.01)
(52) U.S. Cl. ........................................................ 424/428
(58) Field of Classification Search .................. None
See application file for complete search history.

(56) References Cited

U.S. PATENT DOCUMENTS

| | | | | |
|---|---|---|---|---|
| 3,986,510 | A | 10/1976 | Higuchi | 128/260 |
| 4,863,457 | A | 9/1989 | Lee | 604/891.1 |
| 4,966,849 | A | 10/1990 | Vallee | 435/199 |
| 4,997,652 | A | 3/1991 | Wong | 424/428 |
| 5,164,188 | A | 11/1992 | Wong | 428/428 |
| 5,330,992 | A | 7/1994 | Eissenstat | 514/312 |
| 5,443,505 | A | 8/1995 | Wong | 623/6 |
| 5,501,856 | A | 3/1996 | Ohtori | 424/428 |
| 5,543,156 | A * | 8/1996 | Roorda et al. | 424/484 |
| 5,766,242 | A | 6/1998 | Wong | 623/66 |
| 5,824,072 | A | 10/1998 | Wong | 623/6 |
| 5,869,079 | A | 2/1999 | Wong | 424/426 |
| 6,046,187 | A | 4/2000 | Berde | 514/180 |
| 6,074,661 | A * | 6/2000 | Olejnik et al. | 424/427 |
| 6,217,895 | B1 | 4/2001 | Guo | 424/484 |
| 6,369,116 | B1 | 4/2002 | Wong | 424/484 |
| 2004/0019098 | A1 | 1/2004 | Andrews | 548/464 |
| 2005/0043706 | A1* | 2/2005 | Eaton et al. | 604/500 |
| 2005/0048099 | A1* | 3/2005 | Shiah et al. | 424/428 |
| 2006/0024350 | A1* | 2/2006 | Varner et al. | 424/427 |

FOREIGN PATENT DOCUMENTS

| | | |
|---|---|---|
| EP | 0 430 539 | 11/1990 |
| EP | 0 488 401 | 11/1991 |
| EP | 0 654 256 | 2/1994 |
| WO | WO 91/15495 | 3/1991 |
| WO | WO 92/21660 | 4/1992 |
| WO | WO 94/10202 | 10/1992 |
| WO | WO 94/03427 | 8/1993 |
| WO | WO 94/14808 | 7/1994 |
| WO | WO 95/13765 | 11/1994 |

OTHER PUBLICATIONS

Frank et al. Controlled release form bioerodible polymers: effect of drug type and polymer composition. Journal of Controlled Release. 2005, 102, 333-344.*
Beeley et al. (Journal of Biomedical Materials Research Part A, 2005, 73A, 437-444).*
Bloch-Michel E. (1992). *Opening address: intermediate uveitis*, In Intermediate Uveitis, Dev. Ophthalmol, W.R.F. Böke et al. editors, Basel: Karger, 23:1-2.

Bodor, N. et al. (1992). A comparison of intraocular pressure elevating activity of loteprednol etabonate and dexamethasone in rabbits, *Current Eye Research* 11:525-30.
Böke, W. (1992). *Clinical picture of intermediate uveitis*, In Intermediate Uveitis, Dev. Ophthalmol. W.R.F. Böke et al. editors, Basel: Karger, 23:20-7.
Bolen, 1993, Oncogen 8: 2025-2031.
Cheng C-K et al. (1995). *Intravitreal sustained-release dexamethasone device in the treatment of experimental uveitis*, Invest. Ophthalmol. Vis. Sci. 36:442-53.
Heller, *Biodegradable Polymers in Controlled Drug Delivery*, in: "CRC Critical Reviews in Therapeutic Drug Carrier Systems", vol. 1. CRC Press, Boca Raton, FL (1987).
Jellinek, et al, Biochemistry 33: 10450-56.
Kendall & Thomas, 1994, Proc. Nat'l Acad. Sci 90: 10705-09.
Kim, et al, 1993, Nature 362: 841-844.
Kinsella, et al, 1992, Exp. Cell Res. 199: 56-62.
Kwak, H.W. and D'Amico, D. J. (1992). *Evaluation of the retinal toxicity and pharmacokinetics of dexamethasone after intravitreal injection*, Arch. Ophthalmol. 110:259-66.
Lee, V.H.L. et al. (1989). *Drug delivery to the posterior segment* Chapter 25 in Retina. T.E. Ogden and A.P. Schachat eds., St. Louis: CV Mosby, vol. 1, pp. 483-498.
Liggins, R. T. and Bent, H. M., *Paclitaxel-loaded poly(L-lactic acid) microspheres 3: blending low and high molecular weight polymers to control morphology and drug release*; International J of Pharmaceutics 282, 61-71 (2004).
Mariani, et al, 1994, Proc. Am. Assoc. Cancer Res. 35: 2268.
Maurice, D.M. (1983). *Micropharmaceutics of the eye*, Ocular Inflammation Ther. 1:97-102.
Olsen, T.W. et al. (1995), *Human scleral permeability: effects of age, cryotherapy, transscleral diode laser, and surgical thinning*, Invest. Ophthalmol. Vis. Sci. 36:1893-1903.
Pinar, V., et al. (1997). *Intraocular inflammation and uveitis* in Basic and Clinical Science Course. Section 9 (1997-1998) San Francisco: American Academy of Ophthalmology, pp. 57-80, 102-103, 152-156.
Plowman et al, 1994, DN&P 7(6): 334-339. Rao, N.A. et al. (1997). Intraocular inflammation and uveitis, in *Basic and Clinical Science Course*. Section 9 (1997-1998) San Francisco: American Academy of Ophthalmology, pp. 57-80, 102-103, 152-156.
Renfro, L and Snow, J.S. (1992). *Ocular effects of topical and systemic steroids*, Dermatologic Clinics 10:505-12.
Schwartz, B. (1966). *The response of ocular pressure to corticosteroids*, Ophthalmol. Clin. North Am. 6:929-89.
Skalka, H.W. and Pichal, J.T. (1980). Effect of corticosteroids on cataract formation, *Arch Ophthalmol* 98:1773-7.
Takano, et al, 1993, Mol. Bio. Cell 4:358A.
Tracy et al., *Biomaterials* 20:1057-1062 (1999).
USP 23; NF 18 (1995) pp. 1790-1798.
Wright, et al, 1992, J. Cellular Phys. 152: 448-57.
Zhou, T, et al. (1998). *Development of a multiple-drug delivery implant for intraocular management of proliferative vitreoretinopathy*, Journal of Controlled Release 55: 281-295.

* cited by examiner

*Primary Examiner* — Johann Richter
*Assistant Examiner* — Jessica Kassa
(74) *Attorney, Agent, or Firm* — Louis V. Wollenberger; Joel B. German; Debra D. Condino

(57) ABSTRACT

A drug delivery system (DDS) comprised of segmented biodegradable implants sized and suitable for implantation in an ocular region or site and methods for treating ocular conditions. The segmented implants provide an extended release of an active agent at a therapeutically effective amount for a period of time between 50 days and one year, or longer, and permit the DDS to have segments that possess individual and different drug release characteristics.

5 Claims, 1 Drawing Sheet

BIODEGRADABLE DRUG DELIVERY SYSTEM

BACKGROUND

This invention relates to drug delivery systems (e.g. implants), as well as to methods for treating ocular conditions with extended or sustained drug release. In particular the present invention relates to implants and methods for treating an ocular condition by implanting into an ocular region or site a drug delivery system comprising a plurality of extended release bioerodible implant segment, each segment comprising an active agent and a bioerodible polymer. The segmented bioerodible implants of this invention have varying and extended release rates to provide for improved kinetics of release of one or more active (therapeutic) agents over time.

An ocular condition can include a disease, aliment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball. An anterior ocular condition is a disease, aliment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves, the conjunctiva, the cornea, the conjunctiva, the anterior chamber, the iris, the posterior chamber (behind the retina but in front of the posterior wall of the lens capsule), the lens or the lens capsule and blood vessels and nerve which vascularize or innervate an anterior ocular region or site. A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, macular degeneration (such as non-exudative age related macular degeneration and exudative age related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitic retinal disease; retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

An anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

The present invention is concerned with and directed to a drug delivery system and methods for the treatment of an ocular condition, such as an anterior ocular condition or a posterior ocular condition or to an ocular condition which can be characterized as both an anterior ocular condition and a posterior ocular condition.

Therapeutic compounds useful for the treatment of an ocular condition can include active agents with, for example, an anti-neoplastic, anti-angiogenesis, kinase inhibition, anticholinergic, anti-adrenergic and/or anti-inflammatory activity.

Macular degeneration, such as age related macular degeneration ("AMD") is the leading cause of blindness in the world. It is estimated that thirteen million Americans have evidence of macular degeneration. Macular degeneration results in a break down the macula, the light-sensitive part of the retina responsible for the sharp, direct vision needed to read or drive. Central vision is especially affected. Macular degeneration is diagnosed as either dry (atrophic) or wet (exudative). The dry form of macular degeneration is more common than the wet form of macular degeneration, with about 90% of AMD patients being diagnosed with dry AMD. The wet form of the disease usually leads to more serious vision loss. Macular degeneration can produce a slow or sudden painless loss of vision. The cause of macular degeneration is not clear. The dry form of AMD may result from the aging and thinning of macular tissues, depositing of pigment in the macula, or a combination of the two processes. With wet AMD, new blood vessels grow beneath the retina and leak blood and fluid. This leakage causes retinal cells to die and creates blind spots in central vision.

Macular edema ("ME") can result in a swelling of the macula. The edema is caused by fluid leaking from retinal blood vessels. Blood leaks out of the weak vessel walls into a very small area of the macula which is rich in cones, the nerve endings that detect color and from which daytime vision depends. Blurring then occurs in the middle or just to the side of the central visual field. Visual loss can progress over a period of months. Retinal blood vessel obstruction, eye inflammation, and age-related macular degeneration have all been associated with macular edema. The macula may also be affected by swelling following cataract extraction. Symptoms of ME include blurred central vision, distorted vision, vision tinted pink and light sensitivity. Causes of ME can include retinal vein occlusion, macular degeneration, diabetic macular leakage, eye inflammation, idiopathic central serous chorioretinopathy, anterior or posterior uveitis, pars planitis, retinitis pigmentosa, radiation retinopathy, posterior vitreous detachment, epiretinal membrane formation, idiopathic juxtafoveal retinal telangiectasia, Nd:YAG capsulotomy or iridotomy. Some patients with ME may have a history of use of topical epinephrine or prostaglandin analogs for glaucoma. The first line of treatment for ME is typically anti-inflammatory drops topically applied.

An anti-inflammatory (i.e. immunosuppressive) agent can be used for the treatment of an ocular condition, such as a posterior ocular condition, which involves inflammation, such as an uveitis or macula edema. Thus, topical or oral glucocorticoids have been used to treat uveitis. A major problem with topical and oral drug administration is the inability of the drug to achieve an adequate (i.e. therapeutic) intraocular concentration. See e.g. Bloch-Michel E. (1992). *Opening address: intermediate uveitis*, In Intermediate Uveitis, Dev.

Ophthalmol, W. R. F. Böke et al. editors, Basel: Karger, 23:1-2; Pinar, V., et al. (1997). *Intraocular inflammation and uveitis"* In Basic and Clinical Science Course. Section 9 (1997-1998) San Francisco: American Academy of Ophthalmology, pp. 57-80, 102-103, 152-156; Böke, W. (1992). *Clinical picture of intermediate uveitis*, In Intermediate Uveitis, Dev. Ophthalmol. W. R. F. Böke et al. editors, Basel: Karger, 23:20-7; and Cheng C-K et al. (1995). *Intravitreal sustained-release dexamethasone device in the treatment of experimental uveitis*, Invest. Ophthalmol. Vis. Sci. 36:442-53.

Systemic glucocorticoid administration can be used alone or in addition to topical glucocorticoids for the treatment of uveitis. However, prolonged exposure to high plasma concentrations (administration of 1 mg/kg/day for 2-3 weeks) of steroid is often necessary so that therapeutic levels can be achieved in the eye.

Unfortunately, these high drug plasma levels commonly lead to systemic side effects such as hypertension, hyperglycemia, increased susceptibility to infection, peptic ulcers, psychosis, and other complications. Cheng C-K et al. (1995). *Intravitreal sustained-release dexamethasone device in the treatment of experimental uveitis*, Invest. Ophthalmol. Vis. Sci. 36:442-53; Schwartz, B. (1966). *The response of ocular pressure to corticosteroids*, Ophthalmol. Clin. North Am. 6:929-89; Skalka, H. W. et al. (1980). *Effect of corticosteroids on cataract formation*, Arch Ophthalmol 98:1773-7; and Renfro, L. et al. (1992). *Ocular effects of topical and systemic steroids,* Dermatologic Clinics 10:505-12.

Additionally, delivery to the eye of a therapeutic amount of an active agent can be difficult, if not impossible, for drugs with short plasma half-lives since the exposure of the drug to intraocular tissues is limited. Therefore, a more efficient way of delivering a drug to treat a posterior ocular condition is to place the drug directly in the eye, such as directly into the vitreous. Maurice, D. M. (1983). *Micropharmaceutics of the eye*, Ocular Inflammation Ther. 1:97-102; Lee, V. H. L. et al. (1989). *"Drug delivery to the posterior segment"* Chapter 25 In Retina. T. E. Ogden and A. P. Schachat eds., St. Louis: C V Mosby, Vol. 1, pp. 483-98; and Olsen, T. W. et al. (1995). *Human scleral permeability: effects of age, cryotherapy, transscleral diode laser, and surgical thinning*, Invest. Ophthalmol. Vis. Sci. 36:1893-1903.

Techniques such as intravitreal injection of a drug have shown promising results, but due to the short intraocular half-life of active agent, such as glucocorticoids (approximately 3 hours), intravitreal injections must be frequently repeated to maintain a therapeutic drug level. In turn, this repetitive process increases the potential for side effects such as retinal detachment, endophthalmitis, and cataracts. Maurice, D. M. (1983). *Micropharmaceutics of the eye*, Ocular Inflammation Ther. 1:97-102; Olsen, T. W. et al. (1995), *Human scleral permeability: effects of age, cryotherapy, transscleral diode laser, and surgical thinning*, Invest. Ophthalmol. Vis. Sci. 36:1893-1903; and Kwak, H. W. and D'Amico, D. J. (1992). *Evaluation of the retinal toxicity and pharmacokinetics of dexamethasone after intravitreal injection*, Arch. Ophthalmol. 110:259-66.

Additionally, topical, systemic, and periocular glucocorticoid treatment must be monitored closely due to toxicity and the long-term side effects associated with chronic systemic drug exposure sequelae. Rao, N. A. et al. (1997). *Intraocular inflammation and uveitis, In Basic and Clinical Science Course*. Section 9 (1997-1998) San Francisco: American Academy of Ophthalmology, pp. 57-80, 102-103, 152-156; Schwartz, B. (1966). *The response of ocular pressure to corticosteroids, Ophthalmol Clin North Am* 6:929-89; Skalka, H. W. and Pichal, J. T. (1980). *Effect of corticosteroids on cataract formation, Arch Ophthalmol* 98:1773-7; Renfro, L and Snow, J. S. (1992). *Ocular effects of topical and systemic steroids*, Dermatologic Clinics 10:505-12; Bodor, N. et al. (1992). *A comparison of intraocular pressure elevating activity of loteprednol etabonate and dexamethasone in rabbits, Current Eye Research* 11:525-30.

U.S. Pat. No. 6,217,895 discusses a method of administering a corticosteroid to the posterior segment of the eye, but does not disclose a bioerodible implant.

U.S. Pat. No. 5,501,856 discloses controlled release pharmaceutical preparations for intraocular implants to be applied to the interior of the eye after a surgical operation for disorders in retina/vitreous body or for glaucoma.

U.S. Pat. No. 5,869,079 discloses combinations of hydrophilic and hydrophobic entities in a biodegradable sustained release implant, and describes a polylactic acid polyglycolic acid (PLGA) copolymer implant comprising dexamethasone. As shown by in vitro testing of the drug release kinetics, the 100-120 μg 50/50 PLGA/dexamethasone implant disclosed did not show appreciable drug release until the beginning of the fourth week, unless a release enhancer, such as HPMC was added to the formulation.

U.S. Pat. No. 5,824,072 discloses implants for introduction into a suprachoroidal space or an avascular region of the eye, and describes a methylcellulose (i.e. non-biodegradable) implant comprising dexamethasone. WO 9513765 discloses implants comprising active agents for introduction into a suprachoroidal or an avascular region of an eye for therapeutic purposes.

U.S. Pat. Nos. 4,997,652 and 5,164,188 disclose biodegradable ocular implants comprising microencapsulated drugs, and describes implanting microcapsules comprising hydrocortisone succinate into the posterior segment of the eye.

U.S. Pat. No. 5,164,188 discloses encapsulated agents for introduction into the suprachoroid of the eye, and describes placing microcapsules and plaques comprising hydrocortisone into the pars plana. U.S. Pat. Nos. 5,443,505 and 5,766,242 discloses implants comprising active agents for introduction into a suprachoroidal space or an avascular region of the eye, and describes placing microcapsules and plaques comprising hydrocortisone into the pars plana.

Zhou et al. disclose a multiple-drug implant comprising 5-fluorouridine, triamcinolone, and human recombinant tissue plasminogen activator for intraocular management of proliferative vitreoretinopathy (PVR). Zhou, T, et al. (1998). *Development of a multiple-drug delivery implant for intraocular management of proliferative vitreoretinopathy*, Journal of Controlled Release 55:281-295.

U.S. Pat. No. 6,046,187 discusses methods and compositions for modulating local anesthetic by administering one or more glucocorticosteroid agents before, simultaneously with or after the administration of a local anesthetic at a site in a patient.

U.S. Pat. No. 3,986,510 discusses ocular inserts having one or more inner reservoirs of a drug formulation confined within a bioerodible drug release rate controlling material of a shape adapted for insertion and retention in the "sac of the eye," which is indicated as being bounded by the surfaces of the bulbar conjunctiva of the sclera of the eyeball and the palpebral conjunctiva of the eyelid, or for placement over the corneal section of the eye.

U.S. Pat. No. 6,369,116 discusses an implant with a release modifier inserted in a scleral flap.

EP 0 654256 discusses use of a scleral plug after surgery on a vitreous body, for plugging an incision.

U.S. Pat. No. 4,863,457 discusses the use of a bioerodible implant to prevent failure of glaucoma filtration surgery by positioning the implant either in the subconjunctival region between the conjunctival membrane overlying it and the sclera beneath it or within the sclera itself within a partial thickness sclera flap.

EP 488 401 discusses intraocular implants, made of certain polylactic acids, to be applied to the interior of the eye after a surgical operation for disorders of the retina/vitreous body or for glaucoma.

EP 430539 discusses use of a bioerodible implant which is inserted in the suprachoroid.

It is known that PLGA co-polymer formulations of a bioerodible polymer comprising an active agent typically release the active agent with a characteristic sigmoidal release profile (as viewed as time vs percent of total active agent released), that is after a relatively long initial lag period (the first release phase) when little if any active agent is released, there is a high positive slope period when most of the active agent is released (the second release phase) followed by another near horizontal (third) release phase, when the drug release reaches a plateau.

It is known in the art that polymer types may be blended to optimize drug release kinetics. See, Liggins, R. T. and Bent, H. M., *Paclitaxel-loaded poly(L-lactic acid) microspheres 3: blending low and high molecular weight polymers to control morphology and drug release*; International J of Pharmaceutics 282, 61-71 (2004). However, limitations in current technology become apparent when attempting to sustain a zero order release of a drug at a therapeutically effective concentration for as long as three to six months. In the case of highly water-soluble drugs such as certain proteins or oligonucleotides, polymer loading is usually limited to below 20% w/w due to undesirably high burst release profiles. Excessive burst release of 30-80% of the drug payload within one or two days not only precludes extended release by wasting drug, but may also result in undesirable biological effects. Such adverse effects may include drug cytotoxicities, biological accommodation involving up or down regulation of specific drug receptors, or off-targeting of inhibitors such as siRNAs. Other limitations of the current drug delivery systems include the inability to engineer a "drug holiday" during which time no drug is released for safety reasons and the inability to independently control the release profiles of two or more drugs, without requiring multiple injections.

Thus, there is a need for a therapeutically effective extended release implant for the treatment of an ocular condition, such as posterior ocular condition. In particular, there is a need for effective delivery over an extended duration, for example, time periods extending up to 60 days, 90 days, 120 days, 6 months, 8 months, 12 months or more, preferably with maintenance of a therapeutic drug level at a desired posterior ocular region or site and with flexible or adjustable drug release characteristics/profiles, optionally including one or more "drug holidays" during which time no drug is released to the patient. Such extended and flexible delivery of one or more active agents can be advantageous to prevent recurrence of the inflammatory or other posterior ocular condition treated. It can also minimize the number of surgical interventions required by the patient over time to treat the condition, as compared to the use of prior implants, such as those having shorter release profiles and/or consistent release profiles.

SUMMARY

The present invention meets these and other needs and provides for a drug delivery system that comprises segmented bioerodible implants that can provide for flexible, separate and independent drug release characteristics amongst the individual segments, thereby facilitating extended drug release for up to three to six months while avoiding high drug loading or excessive burst release, but permitting variations in drug release profiles.

Definitions

The following terms as used herein have the following meanings:

"About" means approximately or nearly and in the context of a numerical value or range set forth herein means ±10% of the numerical value or range recited or claimed.

"Active agent" and "drug" are used interchangeably and refer to any substance used to treat an ocular condition.

"Bioerodible polymer" means a polymer which degrades in vivo, and wherein erosion of the polymer over time is required to achieve the active agent release kinetics according to the present invention. Thus, hydrogels such as methylcellulose which act to release drug through polymer swelling are specifically excluded from the term "bioerodible (or biodegradable) polymer". The words "bioerodible" and "biodegradable" are synonymous and are used interchangeably herein.

"Cumulative release profile" means to the cumulative total percent of an active agent released from an implant into an ocular region or site in vivo over time or into a specific release medium in vitro over time.

"Extended" as in "extended period" or "extended release" means for a period of time greater than thirty days, preferably for at least 50 days (i.e. for a period of time from 50 days to 365 days), and most preferably for at least 60 days. An extended release can persist for a year or more.

"Glaucoma" means primary, secondary and/or congenital glaucoma. Primary glaucoma can include open angle and closed angle glaucoma. Secondary glaucoma can occur as a complication of a variety of other conditions, such as injury, inflammation, vascular disease and diabetes.

"Inflammation-mediated" in relation to an ocular condition means any condition of the eye which can benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic ophthalmia, Vogt Koyanagi-Harada (VKH) syndrome, histoplasmosis, and uveal diffusion.

"Injury" or "damage" are interchangeable and refer to the cellular and morphological manifestations and symptoms resulting from an inflammatory-mediated condition, such as, for example, inflammation.

"Measured under infinite sink conditions in vitro," means assays to measure drug release in vitro, wherein the experiment is designed such that the drug concentration in the receptor medium never exceeds 5% of saturation. Examples of suitable assays may be found, for example, in USP 23; NF 18 (1995) pp. 1790-1798.

"Ocular condition" means a disease, aliment or condition which affects or involves the eye or one or the parts or regions of the eye, such as a retinal disease. The eye includes the eyeball and the tissues and fluids which constitute the eyeball, the periocular muscles (such as the oblique and rectus muscles) and the portion of the optic nerve which is within or adjacent to the eyeball.

"Plurality" means two or more.

"Posterior ocular condition" means a disease, ailment or condition which affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerve which vascularize or innervate a posterior ocular region or site.

"Steroidal anti-inflammatory agent" and "glucocorticoid" are used interchangeably herein, and are meant to include steroidal agents, compounds or drugs which reduce inflammation when administered at a therapeutically effective level.

"Substantially" in relation to the release profile or the release characteristic of an active agent from a bioerodible implant as in the phrase "substantially continuous rate" of the active agent release rate from the implant means, that the rate of release (i.e. amount of active agent released/unit of time) does not vary by more than 100%, and preferably does not vary by more than 50%, over the period of time selected (i.e. a number of days). "Substantially" in relation to the blending, mixing or dispersing of an active agent in a polymer, as in the phrase "substantially homogenously dispersed" means that there are no or essentially no particles (i.e. aggregations) of active agent in such a homogenous dispersal.

"Suitable for insertion (or implantation) in (or into) an ocular region or site" with regard to an implant, means an implant which has a size (dimensions) such that it can be inserted or implanted without causing excessive tissue damage and without unduly physically interfering with the existing vision of the patient into which the implant is implanted or inserted.

"Therapeutic levels" or "therapeutic amount" means an amount or a concentration of an active agent that has been locally delivered to an ocular region that is appropriate to safely treat an ocular condition so as to reduce or prevent a symptom of an ocular condition.

In one variation, the present invention provides for a drug delivery system (DDS) for treating conditions of the eye that comprises a segmented DDS, each segment comprising a bioerodible implant, each bioerodible implant having a unique drug release profile. In certain variations, this implant system can include three or more implants, each of which is formed from a separate poly(lactide) (i.e. PLA) polymer or poly(lactide-co-glycolide) (i.e. PLGA) copolymer, different polymer blends, or similar polymer blends but with different excipients (in kind or amount) to provide different drug release profiles.

In other variations, bioerodible implants according to the present invention are prepared using two or more different bioerodible polymers each having different release characteristics. In one variation, a first quantity of the drug or active agent is blended with a first polymer composition and the resultant material is extruded into an implant segment and a second quantity of the same or different drug or active agent is blended with a different polymer composition to form a second bioerodible implant segment. The resultant implant segments have different release profiles. The implant segments can be prepared and administered as individual segments, or can be combined into a single segmented DDS, wherein the individual segments are encased within an external matrix, whereby the individual segments separated from each other immediately following injection into the patient, such as into the patient's eye.

The invention encompasses a drug delivery system for treating an ocular condition, the drug delivery system can comprise: (a) at least two bioerodible implant segments suitable for insertion into an ocular region or site, each bioerodible implant segment comprising; (i) an active agent, and; (ii) a bioerodible polymer, wherein each bioerodible implant segment can release a therapeutic level of the active agent into the ocular region or site for a period time between about 30 days and about 1 year and wherein at least one of the implant segments has a drug release profile that is different from at least one other segment. The bioerodible implant segments can release the therapeutic level of the active agent into the ocular region or site at a substantially continuous rate in vivo for the desired period of time. The DDS comprising segments of different drug release profiles can release a therapeutic level of the active agent into the ocular region or site at a substantially continuous rate upon implantation in the vitreous for a period time between about 50 days and about 1 year or can include so-called "drug holidays" wherein no drug is released to the ocular region.

The bioerodible implant can have a weight between about 1 µg and about 100 mg and no dimension less than about 0.1 mm and no dimension greater than about 20 mm.

A drug delivery system of claim within the scope of the invention can comprise a plurality of bioerodible implant segments. The active agent can be substantially homogenously dispersed within the bioerodible polymer or the active agent can be associated with the bioerodible polymer in the form of particles of active agent and bioerodible polymer.

The drug delivery system of the invention can comprise: (a) a plurality of bioerodible implant segments implantable in a posterior ocular region or site, each segment comprising; (i) an active agent, and; (ii) a bioerodible polymer, wherein the plurality of segments can substantially continuously, or in any desired pattern or profile, release in vivo a therapeutic level of the active agent or a plurality of different active agents, for a period time between about 5 days and about 1 year. This drug delivery system can comprise: (a) a first segment with a first release characteristic, and; (b) a second implant with a second release characteristic, wherein the first and second release characteristics differ. The release profile of the drug delivery system can correspond to the sum of the first and second release profiles. Alternatively, this drug delivery system can comprise: (a) a first segment with a first release characteristic, (b) a second segment with a second release characteristic, and; (c) a third implant with a third release characteristic. The release profile of the drug delivery system can correspond to the sum of the first, second and third release profiles. Thus, the drug deliver system can comprise first, second and third bioerodible segments, wherein the first segment comprises a first polymer component; the second segment comprises a second polymer component, and the third segment comprises a third polymer component, wherein the first, second and third polymer components differ with respect to the mixture of the blended polymers (by type and/or percent mixture).

One method for making an extended release bioerodible implant for treating an ocular condition can be by: (a) blending and extruding first active agent and a first bioerodible polymer composition to form a first implant segment; (b) blending and extruding a second active agent with a second bioerodible polymer composition, to form a second implant segment, wherein the implants can release a therapeutic level of the active agents at a substantially continuous rate for a period time between about 50 days and about 1 year, but with different profiles with respect to each other.

The first active agent and the second active agent can be the same active agent or the first active agent and the second active agent can be different active agents. As well, the first polymer composition and the second polymer composition can comprise the same polymer but with different excipients (in kind and/or amount) or the first polymer composition and the second polymer composition can comprise different polymers, whereby the drug release profiles can be adjusted by adjusting the ratio of monomers in the polymer blend and/or by, including appropriate excipients, or amounts of excipients, to modify the drug release characteristics.

A method for treating an ocular condition according to our invention can comprise implanting into an ocular region or site a drug delivery system set forth herein.

Our invention includes a drug delivery system for treating an ocular condition. The drug delivery system can comprise a bioerodible implant having a plurality of segments, wherein each of the segments comprises an active agent and (ii) a bioerodible polymer; at least some of the segments have drug release characteristics different from other segments; and the segments are joined together (or otherwise associated with each other as separate implants which are implanted together) in a manner to permit separation from each other in situ into individual segments following intraocular implantation of the drug delivery system into a patient.

Our invention also includes a drug delivery system for treating an ocular condition which comprises a bioerodible implant comprising a plurality of rod-shaped segments, wherein each of the segments comprises (i) an active agent for treating the ocular condition and (ii) a bioerodible polymer; at least some of the segments have drug release characteristics different from other that of other segments; the segments are joined (or associated) together at the ends thereof to form a contiguous rod-shaped implant; and the segments are joined at the ends thereof in a manner to permit separation of the segments from each other in situ into individual segments following implantation into the ocular region of a patient.

Our invention also encompasses a drug delivery system for treating an ocular condition which comprises a bioerodible implant comprising a plurality of rod-shaped segments, wherein each of the segments comprises (i) an active agent for treating the ocular condition and (ii) a bioerodible polymer; at least some of the segments have drug release characteristics different from other of the segments; and at least some of the segments having at least one end thereof having a cut surface that is at an angle to the longitudinal axis of less than 90° or having at least one end which is of beveled shape.

The individual segments can be are joined together at the ends thereof to form a contiguous rod-shaped implant having a longitudinal axis, the segments being joined together in a matrix comprised of a bioerodible polymer in a manner to permit separation of the segments from each other in situ into individual segments following implantation into the ocular region of a patient.

The bioerodible polymer of our drug delivery system can comprise at least one member selected from the group consisting of poly(lactide) polymers and poly(lactide-co-glycolide) copolymers. The implants of our drug delivery can further comprise at least one excipient that modifies the erosion characteristics of the bioerodible polymer. The excipient can be a long chain fatty alcohol, cholesterol, or high molecular weight polyethylene glycol polymers.

The bioerodible polymer can be a poly(D,L-lactide-co-glycolide) copolymer with a monomer ratio in the range of 50:50 to 85:15. Preferably, at least one of the segments can release all active ingredient within one week of implantation and at least one of the segments can begin releasing the active ingredient after one week post-implantation. Alternately, a at least one of the segments can begin releasing active ingredient at 12 weeks post-implantation or at least one of the segments releases the active ingredient from 3 to 6 months post-implantation.

The active ingredient can be released from one of the segments within the first week after implantation, but with no drug released from any of the segments for some period of time after the first week post-implantation.

At least some of the segments can comprise a first active ingredient and other of the segments can comprise a second active ingredient. Each of the segments can have drug release characteristics different from all of the other of the segments that comprise the implant.

The active ingredient can be a steroid, an anti-inflammatory compound, or an anti-angiogenesis compound. The active ingredient can, for example, be methotrexate, retinoic acid, aspirin, diclofenac, flurbiprofen, ibuprofen, ketorolac, naproxen, uprofen, dexamethasone, cortisone, fluocinolone, hydrocortisone, methylprednisolone, prednisolone, prednisone, or triamcinolone.

Our invention includes a method of manufacturing a drug delivery system which comprises a bioerodible implant by: blending a first active agent with a first bioerodible polymer to form a first active agent polymer mixture; forming the first active agent polymer mixture into a rod shaped first implant segment having a longitudinal axis; blending a second active agent with a second bioerodible polymer to form a second active agent polymer mixture; and forming at least some of the segments with at least one end thereof having a cut surface that is at an angle to the longitudinal axis of less than 90° or has a beveled shape. The segments can be joined at the ends thereof to permit separation from each other in situ into individual segments following implantation into a patient. Each of the segments can be formed with at least one end having a cut surface that is at an angle to the longitudinal axis of less than 90° or one end having a beveled shaped surface. The bioerodible polymer can be a poly(lactide) polymer and poly(lactide-co-glycolide) copolymer. At least one excipient that modifies the erosion characteristics of the bioerodible polymer can be blended with the active agent and the bioerodible polymer.

DRAWINGS

DESCRIPTION

Figure 1:
FIG. 1 depicts a typical drug delivery system in the prior art.

The present invention is based upon the discovery of a drug delivery system (DDS) comprised of segmented bioerodible implants whereby each segment can release a therapeutic amount of an active agent for an extended period of time to treat an ocular condition with each segment capable of having an independent drug release profile that is different from the other segments. The present invention encompasses biodegradable ocular implants and implant systems and methods of using such implants and implant systems for treating ocular conditions. The implants can be formed to be monolithic, that is the active agent is homogenously distributed or dispersed throughout the biodegradable polymer matrix. Additionally, the implants can be formed to release an active agent into an ocular region of the eye over various extended release time periods. Thus, the active agent can be released from implants made according to the present invention for an extended periods of time of approximately 60 days or more, 90 days or more, 120 days or more, 6 months or more, 8 months or more or 12 months or more.

Biodegradable Implants for Treating an Ocular Condition

The implants of the present invention can include an active agent mixed with or dispersed within a biodegradable polymer. The implant compositions can vary according to the preferred drug release profile, the particular active agent used, the ocular condition being treated, and the medical history of the patient. Active agents that may be used include, but are not limited to (either by itself in an implant within the scope of the present invention or in combination with another active agent): ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites, antiangiogenic agents, tyrosine kinase inhibitors, antibiotics such as aminoglycosides such as gentamycin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline; quinolones such as ciproflaxin, etc.; sulfonamides such as chloramine T; and sulfones such as sulfanilic acid as the hydrophilic entity, anti-viral drugs, e.g. acyclovir, gancyclovir, vidarabine, azidothymidine, dideoxyinosine, dideoxycytosine, dexamethasone, ciproflaxin, water soluble antibiotics, such as acyclovir, gancyclovir, vidarabine, azidothymidine, dideoxyinosine, dideoxycytosine; epinephrine; isoflurophate; adriamycin; bleomycin; mitomycin; ara-C; actinomycin D; scopolamine; and the like, analgesics, such as codeine, morphine, ketorolac, naproxen, etc., an anesthetic, e.g. lidocaine; .beta.-adrenergic blocker or ⊕-adrenergic agonist, e.g. ephedrine, epinephrine, etc.; aldose reductase inhibitor, e.g. epalrestat, ponalrestat, sorbinil, tolrestat; antiallergic, e.g. cromolyn, beclomethasone, dexamethasone, and flunisolide; colchicine, anthelmintic agents, e.g. ivermectin and suramin sodium; antiamebic agents, e.g. chloroquine and chlortetracycline; and antifungal agents, e.g. amphotericin, etc., anti-angiogenesis compounds such as anecortave acetate, retinoids such as tazarotene, anti-glaucoma agents, such as brimonidine (Alphagan and Alphagan P), acetazolamide, bimatoprost (Lumigan), timolol, mebefunolol; memantine; alpha-2 adrenergic receptor agonists; 2-methoxyestradiol; anti-neoplastics, such as vinblastine, vincristine, interferons; alpha, beta and gamma, antimetabolites, such as folic acid analogs, purine analogs, and pyrimidine analogs; immunosuppressants such as azathioprine, cyclosporine and mizoribine; miotic agents, such as carbachol, mydriatic agents such as atropine, etc., protease inhibitors such as aprotinin, camostat, gabexate, vasodilators such as bradykinin, etc., and various growth factors, such epidermal growth factor, basic fibroblast growth factor, nerve growth factors, and the like.

In one variation the active agent is methotrexate. In another variation, the active agent is a retinoic acid. In another variation, the active agent is an anti-inflammatory agent such as a nonsteroidal anti-inflammatory agent. Nonsteroidal anti-inflammatory agents that may be used include, but are not limited to, aspirin, diclofenac, flurbiprofen, ibuprofen, ketorolac, naproxen, and suprofen. In a further variation, the anti-inflammatory agent is a steroidal anti-inflammatory agent, such as dexamethasone.

Steroidal Anti-Inflammatory Agents

The steroidal anti-inflammatory agents that may be used in the ocular implants include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives.

In one embodiment, cortisone, dexamethasone, fluocinolone, hydrocortisone, methylprednisolone, prednisolone, prednisone, and triamcinolone, and their derivatives, are preferred steroidal anti-inflammatory agents. In another preferred variation, the steroidal anti-inflammatory agent is dexamethasone. In another variation, the biodegradable implant includes a combination of two or more steroidal anti-inflammatory agents.

The active agent, such as a steroidal anti-inflammatory agent, can comprise from about 10% to about 90% by weight of the implant. In one variation, the agent is from about 40% to about 80% by weight of the implant. In one embodiment, the agent comprises about 60% by weight of the implant. In another embodiment of the present invention, the agent can comprise about 50% by weight of the implant.

Biodegradable Polymers

In one variation, the active agent can be homogeneously dispersed in the biodegradable polymer of the implant. The implant can be made, for example, by a sequential or double extrusion method. The selection of the biodegradable polymer used can vary with the desired release kinetics, patient tolerance, the nature of the disease to be treated, and the like. Polymer characteristics that are considered include, but are not limited to, the biocompatibility and biodegradability at the site of implantation, compatibility with the active agent of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. In one variation, the biodegradable polymer matrix comprises about 40% to 50% by weight of the implant.

Biodegradable polymers which can be used include, but are not limited to, polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers can be crosslinked or non-crosslinked. If crosslinked, they are usually not more than lightly crosslinked, and are less than 5% crosslinked, usually less than 1% crosslinked.

For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen can be present as amide, cyano, and amino. An exemplary list of biodegradable polymers that can be used are described in Heller, *Biodegradable Polymers in Controlled Drug Delivery*, In: "CRC Critical Reviews in Therapeutic Drug Carrier Systems", Vol. 1. CRC Press, Boca Raton, Fla. (1987).

Of particular interest are polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. In certain variations, 25/75 PLGA and/or 50/50 PLGA and/or 75/25 PLGA, and/or 85/15 PLGA copolymers are used. In other variations, PLGA copolymers are used in conjunction with polylactide polymers.

Biodegradable polymer matrices that include mixtures of hydrophilic and hydrophobic ended PLGA may also be employed, and are useful in modulating polymer matrix degradation rates. Hydrophobic ended (also referred to as capped or end-capped) PLGA has an ester linkage hydrophobic in nature at the polymer terminus. Typical hydrophobic end groups include, but are not limited to alkyl esters and aromatic esters. Hydrophilic ended (also referred to as uncapped) PLGA has an end group hydrophilic in nature at the polymer terminus. PLGA with a hydrophilic end groups at the polymer terminus degrades faster than hydrophobic ended PLGA because it takes up water and undergoes hydrolysis at a faster rate (Tracy et al., *Biomaterials* 20:1057-1062 (1999)). Examples of suitable hydrophilic end groups that may be incorporated to enhance hydrolysis include, but are not limited to, carboxyl, hydroxyl, and polyethylene glycol. The specific end group will typically result from the initiator employed in the polymerization process. For example, if the initiator is water or carboxylic acid, the resulting end groups will be carboxyl and hydroxyl. Similarly, if the initiator is a monofunctional alcohol, the resulting end groups will be ester or hydroxyl.

Excipients

The segments are preferably formulated with different polymer blends, or of similar blends but with different excipients, and are designed to erode at different rates in situ. The present invention offers the formulator additional degrees of freedom, thereby facilitating extended release for as long as three to six months while avoiding high drug loading and excessive burst release of very water-soluble drugs.

Excipients that may be incorporated into some or all of these DDS segments include poorly water-soluble molecules such as long chain fatty alcohols, cholesterol, or high molecular weight polyethylene glycol polymers. These excipients may fill voids and pores in the polymer matrix and retard undesirable burst release of water-soluble drugs. Concentrations of certain excipients in one or more segments can dramatically slow drug release rates, an effect which is advantageous for designing optimum sustained release kinetics.

Aliphatic alcohols (also known synonymously as fatty alcohols or as long chain alcohols or as long chain fatty alcohols) are predominately straight chain organic molecules with an even number of carbon atoms derived from natural fats and oils. Aliphatic alcohols can be converted to or derived from fatty acids and fatty aldehydes. It is known to use the smaller aliphatic alcohols as additives in cosmetics and food, and as industrial solvents. Some larger aliphatic alcohols have been used as biofuels.

Due to their amphipathic nature, aliphatic alcohols can behave as nonionic surfactants and find use as emulsifiers, emollients and thickeners in the cosmetics and food industries. Additionally, aliphatic alcohols are a common component of waxes, mostly as esters with fatty acids but also as alcohols themselves.

Natural Fatty alcohols can be derived from natural fats and oils and are high molecular straight chain primary alcohols. They include lauryl (C12), myristyl (C14), Cetyl (or palmityl: C16), stearyl (C18), Oleyl (C18, unsaturated), and Linoleyl (C18, polyunsaturated) alcohols. Synthetic fatty alcohols equivalent physically and chemically to natural alcohols can be obtained from oleochemical sources such as coconut and palm kernel oil.

Aliphatic alcohols include:

capryl alcohol (1-octanol)—8 carbon atoms pelargonic alcohol (1-nonanol)—9 carbon atoms capric alcohol (1-decanol, decyl alcohol)—10 carbon atoms lauryl alcohol (1-dodecanol)—12 carbon atoms myristyl alcohol (1-tetradecanol)—14 carbon atoms cetyl alcohol (1-hexadecanol: $C_{16}H_{34}O$)—16 carbon atoms and has a molecular weight of 242.45 palmitoleyl alcohol (cis-9-hexadecan-1-ol)—16 carbon atoms, unsaturated, $CH_3(CH_2)_5CH=CH(CH_2)_8OH$ stearyl alcohol (1-octadecanol)—18 carbon atoms isostearyl alcohol (16-methylheptadecan-1-ol)—18 carbon atoms, branched, $(CH_3)_2CH-(CH_2)_{15}OH$ elaidyl alcohol (9E-octadecen-1-ol)—18 carbon atoms, unsaturated, $CH_3(CH_2)_7CH=CH(CH_2)_8OH$ oleyl alcohol (cis-9-octadecen-1-ol)—18 carbon atoms, unsaturated linoleyl alcohol (9Z, 12Z-octadecadien-1-ol)—18 carbon atoms, polyunsaturated elaidolinoleyl alcohol (9E, 12E-octadecadien-1-ol)—18 carbon atoms, polyunsaturated linolenyl alcohol (9Z, 12Z, 15Z-octadecatrien-1-ol)—18 carbon atoms, polyunsaturated elaidolinolenyl alcohol (9E, 12E, 15-E-octadecatrien-1-ol)—18 carbon atoms, polyunsaturated ricinoleyl alcohol (12-hydroxy-9-octadecen-1-ol)—18 carbon atoms, unsaturated, diol, $CH_3(CH_2)_5CH(OH)CH_2CH=CH(CH_2)_8OH$ arachidyl alcohol (1-eicosanol)—20 carbon atoms behenyl alcohol (1-docosanol)—22 carbon atoms erucyl alcohol (cis-13-docosen-1-ol)—22 carbon atoms, unsaturated, $CH_3(CH_2)_7CH=CH(CH_2)_{12}OH$ lignoceryl alcohol (1-tetracosanol)—24 carbon atoms ceryl alcohol (1-hexacosanol)—26 carbon atoms montanyl alcohol, cluytyl alcohol (1-octacosanol)—28 carbon atoms myricyl alcohol, melissyl alcohol (1-triacontanol)—30 carbon atoms, and;

geddyl alcohol (1-tetratriacontanol)—34 carbon atoms.

Behenyl alcohol, lignoceryl alcohol, ceryl alcohol, 1-heptacosanol, montanyl alcohol, 1-nonacosanol, myricyl alcohol, 1-dotriacontanol, and geddyl alcohol are together classified as policosanol, with montanyl alcohol and myricyl alcohol being the most abundant.

1-eicosanol (arachidyl alcohol) has the formula $CH_3(CH_2)_{18}CH_2OH$ and a molecular weight of 298.55. Synonyms are 1-Icosanol; Icosan-1-ol; Icosanol; arachidic alcohol; eicosyl alcohol; 1-prydroxyeicosane, and; eicosanol-(1). It is a white solid with a melting point of 64-66° C.

Additional Agents

Other agents may be employed in the formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the formulation.

The biodegradable ocular implants can also include additional hydrophilic or hydrophobic compounds that accelerate or retard release of the active agent. Additionally, release modulators such as those described in U.S. Pat. No. 5,869,079 can be included in the implants. The amount of release modulator employed will be dependent on the desired release profile, the activity of the modulator, and on the release profile of the glucocorticoid in the absence of modulator. Where the buffering agent or release enhancer or modulator is hydrophilic, it may also act as a release accelerator. Hydrophilic additives act to increase the release rates through faster dissolution of the material surrounding the drug particles, which increases the surface area of the drug exposed, thereby increasing the rate of drug diffusion. Similarly, a hydrophobic buffering agent or enhancer or modulator can dissolve more slowly, slowing the exposure of drug particles, and thereby slowing the rate of drug diffusion.

Release Kinetics

An implant within the scope of the present invention can be formulated with particles of an active agent dispersed within a biodegradable polymer matrix. Without being bound by theory, it is believed that the release of the active agent can be achieved by erosion of the biodegradable polymer matrix and by diffusion of the particulate agent into an ocular fluid, e.g., the vitreous, with subsequent dissolution of the polymer matrix and release of the active agent. Factors which influence the release kinetics of active agent from the implant can include such characteristics as the size and shape of the implant, the size of the active agent particles, the solubility of the active agent, the ratio of active agent to polymer(s), the method of manufacture, the surface area exposed, and the erosion rate of the polymer(s). The release kinetics achieved by this form of active agent release are different than that achieved through formulations which release active agents through polymer swelling, such as with crosslinked hydrogels. In that case, the active agent is not released through polymer erosion, but through polymer swelling and drug diffusion, which releases agent as liquid diffuses through the pathways exposed.

The release rate of the active agent can depend at least in part on the rate of degradation of the polymer backbone component or components making up the biodegradable polymer matrix. For example, condensation polymers may be degraded by hydrolysis (among other mechanisms) and therefore any change in the composition of the implant that enhances water uptake by the implant will likely increase the rate of hydrolysis, thereby increasing the rate of polymer degradation and erosion, and thus increasing the rate of active agent release.

The release kinetics of the implants of the present invention can be dependent in part on the surface area of the implants. A larger surface area exposes more polymer and active agent to ocular fluid, causing faster erosion of the polymer matrix and dissolution of the active agent particles in the fluid. Therefore, the size and shape of the implant may also be used to control the rate of release, period of treatment, and active agent concentration at the site of implantation. At equal active agent loads, larger implants will deliver a proportionately larger dose, but depending on the surface to mass ratio, may possess a slower release rate. For implantation in an ocular region, the total weight of the implant preferably ranges, e.g., from about 100 µg to about 15 mg. Alternatively, the implant rages from about 300 µg to about 10 mg, or from about 500 µg to about 5 mg. In a particular embodiment of the present invention the weight of an implant is between about 500 µg and about 2 mg, such as between about 500 µg and about 1 mg.

Segmenting Implants to Affect Release Kinetics

Figure 3:
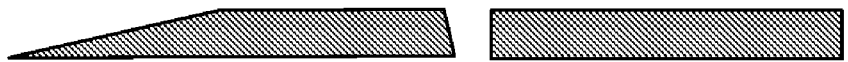
FIG. 3 depicts another segmented drug delivery system implant according to the invention.

According to the invention, the release kinetics can also be altered by producing the implant segments with cut ends that are different from a 90° angle. FIG. 1 shows implant segments prepared in a rod shape with straight ends cut at a 90° angle. Alternatively, one or both ends of an implant segment can be prepared as beveled or cut at less that a 90° angle, as shown in FIG. 3. Of course, segments can be prepared with combinations of different cut end shapes, modified to produce the desired modified kinetic characteristics based upon the altered surface area of the segments. An implant segment end can be angulated so as to facilitate implant segments (when a plurality of implant segments are implanted) easily sliding past one another so that all implant segments can align side by side in the vitreous, instead of the implants aligning as a single line of implants in the vitreous.

The implant segments according to the invention can be prepared and administered as distinct separate and independent segments, or as a single segmented DDS wherein the individual segments are encased in one external matrix. If prepared as a single DDS, the external matrix can comprise quickly erodible PLA or PLGA polymers (such as RG502H, RG503H or RG504H, discussed below) so that immediately upon administration the segments separate from each other. A quickly erodible matrix can also be prepared by incorporation into two matrix of very water soluble molecules (so-called "pore formers") such as mannitol (e.g. 5% w/w).

The bioerodible implants are typically solid, and may be formed as particles, sheets, patches, plaques, films, discs, fibers, rods, and the like, or may be of any size or shape compatible with the selected site of implantation, as long as the implants have the desired release kinetics and deliver an amount of active agent that is therapeutic for the intended medical condition of the eye. The upper limit for the implant size will be determined by factors such as the desired release kinetics, toleration for the implant at the site of implantation, size limitations on insertion, and ease of handling. For example, the vitreous chamber is able to accommodate relatively large rod-shaped implants, generally having diameters of about 0.05 mm to 3 mm and a length of about 0.5 to about 10 mm. In one variation, the rods have diameters of about 0.1 mm to about 1 mm. In another variation, the rods have diameters of about 0.3 mm to about 0.75 mm. In yet a further variation, other implants having variable geometries but approximately similar volumes may also be used.

The proportions of active agent, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the drug delivery device is added to a measured volume of a solution containing 0.9% NaCl in water, where the solution volume will be such that the drug concentration after release is less than 20%, and preferably less than 5%, of saturation. The mixture is maintained at 37° C. and stirred slowly to ensure drug diffusion after bioerosion. The appearance of the dissolved drug as a function of time may be followed by various methods known in the art, such as spectrophotometrically, HPLC, mass spectroscopy, etc.

Therapeutic Use

Examples of ocular conditions which can be treated by the implants and methods of the invention include, but are not limited to, glaucoma, uveitis, macular edema, macular degeneration, retinal detachment, posterior ocular tumors, fungal or viral infections, multifocal choroiditis, diabetic retinopathy, proliferative vitreoretinopathy (PVR), sympathetic opthalmia, Vogt Koyanagi-Harada (VKH) syndrome, histoplasmosis, uveal diffusion, and vascular occlusion. In one variation, the implants are particularly useful in treating such medical conditions as uveitis, macular edema, vascular occlusive conditions, proliferative vitreoretinopathy (PVR), and various other retinopathies.

Methods of Implantation

The biodegradable implants can be inserted into the eye by a variety of methods, including placement by forceps, by trocar, or by other types of applicators, after making an incision in the sclera. In some instances, a trocar or applicator may be used without creating an incision. In a preferred variation, a hand held applicator is used to insert one or more biodegradable implants into the eye. The hand held applicator typically comprises an 18-30 GA stainless steel needle, a lever, an actuator, and a plunger. Suitable devices for inserting an implant or implants into a posterior ocular region or site includes those disclosed in U.S. patent application Ser. No. 10/666,872.

The method of implantation generally first involves accessing the target area within the ocular region with the needle, trocar or implantation device. Once within the target area, e.g., the vitreous cavity, a lever on a hand held device can be depressed to cause an actuator to drive a plunger forward. As the plunger moves forward, it can push the implant or implants into the target area (i.e. the vitreous).

Methods for Making Implants

Various techniques may be employed to make implants within the scope of the present invention. Useful techniques include phase separation methods, interfacial methods, extrusion methods, compression methods, molding methods, injection molding methods, heat press methods and the like.

Choice of the technique, and manipulation of the technique parameters employed to produce the implants can influence the release rates of the drug. Room temperature compression methods result in an implant with discrete microparticles of drug and polymer interspersed. Extrusion methods result in implants with a progressively more homogeneous dispersion of the drug within a continuous polymer matrix, as the production temperature is increased.

The use of extrusion methods allows for large-scale manufacture of implants and results in implants with a homogeneous dispersion of the drug within the polymer matrix. When using extrusion methods, the polymers and active agents that are chosen are stable at temperatures required for manufacturing, usually at least about 50° C. Extrusion methods use temperatures of about 25° C. to about 150° C., more preferably about 60° C. to about 130° C.

Different extrusion methods may yield implants with different characteristics, including but not limited to the homogeneity of the dispersion of the active agent within the polymer matrix. For example, using a piston extruder, a single screw extruder, and a twin screw extruder will generally produce implants with progressively more homogeneous dispersion of the active. When using one extrusion method, extrusion parameters such as temperature, extrusion speed, die geometry, and die surface finish will have an effect on the release profile of the implants produced.

In one variation of producing implants by a piston extrusion methods, the drug and polymer are first mixed at room temperature and then heated to a temperature range of about 60° C. to about 150° C., more usually to about 100° C. for a time period of about 0 to about 1 hour, more usually from about 0 to about 30 minutes, more usually still from about 5 minutes to about 15 minutes, and most usually for about 10 minutes. The implants are then extruded at a temperature of about 60° C. to about 130° C., preferably at a temperature of about 90° C.

In an exemplary screw extrusion method, the powder blend of active agent and polymer is added to a single or twin screw extruder preset at a temperature of about 80° C. to about 130° C., and directly extruded as a filament or rod with minimal residence time in the extruder. The extruded filament or rod is then cut into small implants having the loading dose of active agent appropriate to treat the medical condition of its intended use.

Implant systems according to the invention can include a combination of a number of bioerodible implant segments, each segment having unique polymer compositions and drug release profiles that when co-administered provide for an extended continuous release of drug. Further, the achieved continuous release of drug is both prolonged and distinct from the release profile that would occur with a single implant consisting of a blend of the polymers. For example, to achieve continuous release of at least 120 days, three individual implants made of separate polymer compositions that have fast, medium and slow release characteristics can be employed, with the fast release implant releasing most of the drug from 0-60 days, the medium release implant releasing most of the drug from 60-100 days, and the slow release implant releasing most of the drug from 100 days on. Examples of fast release implants include those made of certain lower molecular weight, fast degradation profile polylactide polymers, such as R104 made by Boehringer Ingelheim GmbH, Germany, which is a poly(D,L-lactide) with a molecular weight of about 3,500. Examples of medium release implants include those made of certain medium molecular weight, intermediate degradation profile PLGA co-polymers, such as RG755 made by Boehringer Ingelheim GmbH, Germany, which is a poly(D,L-lactide-co-glycolide with wt/wt 75% lactide:25% glycolide, a molecular weight of about 40,000 and an inherent viscosity of 0.50 to 0.70 dl/g. Examples of slow release implants include those made of certain other high molecular weight, slower degradation profile polylactide polymers, such as R203/RG755 made by Boehringer Ingelheim GmbH, Germany, for which the molecular weight is about 14,000 for R203 (inherent viscosity of 0.25 to 0.35 dl/g) and about 40,000 for RG755. When administered together, these implants provide for an extend continuous release of drug over a period of at least 120 days in vitro which can result in sustained drug levels (concentration) of at least about 5-10 ng dexamethasone equivalent/mL in the vitreous (i.e. in vivo) for up to about 240 days.

Individual bioerodible implant segments with extended or variable release profiles can also be prepared according to the invention using two or more different bioerodible polymers each having different release characteristics. In one such method, particles of a drug or active agent are blended with a first polymer and extruded to form a filament or rod. This filament or rod is then itself broken first into small pieces and then further ground into particles with a size (diameter) between about 30 μm and about 50 μm, which are then blended with an additional quantities of the drug or active agent and a second polymer. This second mixture is then extruded into filaments or rods which are then cut to the appropriate size to form the final implant. The resultant implant has a release profile different than that of an implant segment created by initially blending the two polymers together and then extruding it. It is posited that formed implant includes initial particles of the drug and first polymer having certain specific release characteristics bound up in the second polymer and drug blend that itself has specific release characteristics that are distinct from the first.

Examples of implants include those formed with RG755, R203, RG503, RG502, RG 502H as the first polymer, and RG502, RG 502H as the second polymer. Other polymers that can be used include PDL (poly(D,L-lactide)) and PDLG (poly(D,L-lactide-co-glycolide)) polymers available from PURAC America, Inc. Lincolnshire, Ill. Poly(caprolactone) polymers can also be used. The characteristics of the specified polymers are (1) RG755 has a molecular weight of about 40,000, a lactide content (by weight) of 75%, and a glycolide content (by weight) of 25%; (2) R203 has a molecular weight of about 14,000, and a lactide content of 100%; (3) RG503 has a molecular weight of about 28,000, a lactide content of 50%, and a glycolide content of 50%; (4) RG502 has a molecular weight of about 11,700 (inherent viscosity of 0.16 to 0.24 dl/g), a lactide content of 50%, and a glycolide content of 50%, and; (5) RG502H has a molecular weight of about 8,500, a lactide content of 50%, a glycolide content of 50% and free acid at the end of polymer chain.

Generally, if inherent viscosity is 0.16 the molecular weight is about 6,300, and if the inherent viscosity is 0.28 the molecular weight is about 20,700. It is important to note that all polymer molecular weights set forth herein are averaged molecular weights in Daltons.

Examples of PLGA-type polymers that may be used for some or all of these segments include, but are not limited to, those shown in Table 1.

TABLE 1

Examples of Useful Biodegradable Polymers

| Polymer Name | Approximate Erosion Time in vivo | Boehringer Ingelheim Catalog Number |
| --- | --- | --- |
| poly(D,L-lactide-co-glycolide) 50:50 | 1 month | RG 502H, 503H, 504H |
| poly(D,L-lactide-co-glycolide) 75:25 | 2 months | RG 752 |
| poly(D,L-lactide-co-glycolide) 85:15 | 3-4 months | LG 857 |

According to our invention continual or substantially continual release of drug at levels corresponding to at least 10 ng/ml of dexamethasone or dexamethasone equivalent for at least 60 days can be achieved.

Figure 2:
FIG. 2 depicts a segmented drug delivery system implant according to the invention.

In one useful embodiment, polymer segments may be simple rod shapes with straight ends cut at a 90° angle (FIG. 2). In another embodiment, the ends are beveled or shaped in a manner that facilitates separation of the segments immediately following injection, for example into the vitreous chamber of an eye (FIG. 3). Such a separation is advantageous to the patient since it avoids or minimizes any obscuration or shadowing in the visual field that commonly occurs upon installation of a single, long cylindrical implant. In addition, separation of polymer segments upon injection facilitates a more uniform diffusion of drug into the vitreous chamber, thereby avoiding high local concentrations of either drug or degraded polymer components (e.g., lactic and glycolic acids), any of which could increase cytotoxicity. Thus, for example, a drug delivery system comprised of a plurality (such as three) segments, each having at least one beveled end, can be administered to a patient's eye with a standard application, and the individual segments will not stay arranged in one longitudinal system in the patient's eye. The individual segments, instead, can move to positions near or next to each other. Administration of a plurality of segments, all having flat ends, tends to result in the administration of a longitudinally continuous line of segments, which can obscure the patient's vision.

A multi-segmented cylindrical device composed of a PLGA polymer has been described (Zhou, T. et al, *Development of a multiple-drug delivery implant for intraocular management of proliferative vitreoretinopathy*, J of Controlled Release 55, 281-295, 1998) that allows for simultaneous, multiple drug release. However, this publication describes a single, long, contiguous cylinder with a series of internal compartments that is impractical for implantation in the vitreous cavity for reasons mentioned above. The present invention allows for controlled delivery of multiple drugs from multiple independent polymer segments, each with its own release kinetics tailored to the therapeutic profile of the active ingredient.

The present invention also allows for the design and preparation of a DDS the provides episodic bursts of drug followed by a drug "holiday" which drug delivery pattern may be advantageous for safety reasons, e.g., when the incorporated drug is a potent steroid. In another useful embodiment, three segments can contain the same drug. For example, Segment #1 provides a loading dose by releasing all incorporated drug within one week post-injection, segment #2 releases all drug between the second and sixth week, and segment #3 starts releasing drug only at 12 weeks. Intentionally, no drug is released between the sixth and twelfth weeks.

In yet another embodiment, segments #1 and #3 can contain drug A while segment #2 contains drug B. By choosing the appropriate polymer blends and excipients, these three segments will release their drug separately and at different, predetermined times.

EXAMPLES

The following examples illustrate aspects and embodiments of the invention.

Example 1

Preparation of Dexamethasone Three Implant Extended Release System

A bioerodible implant system for extended delivery of dexamethasone is made by mixing the active agent dexamethasone (Pharmacia Corp., Peapack, N.J.) separately with each of the following three different polymers:

1. poly (D,L-lactide-co-glycolide) as a 50:50 (wt %/wt %) blend of lactide:glycolide (RG502H, RG503H or RG504H, Boehringer Ingelheim GmbH, Germany), 2. poly(D,L-lactide-co-glycolide) as a 75:25 (wt %/wt %) blend of lactide:glycolide (RG752, Boehringer Ingelheim GmbH, Germany), and;

3. poly (D,L-lactide-co-glycolide) as a 85:15 (wt %/wt %) blend of lactide:glycolide) (LG857, Boehringer Ingelheim GmbH, Germany), so as to obtain three different dexamethasone-polymer mixes.

The polymers noted above are poly(lactide-co-glycolide) co-polymers. The molecular weight of RG755 is about 40,000.

The dexamethasone and one of the three polymers specified above were thoroughly mixed at a ratio of 50/50 by weight ratio of dexamethasone and each of the three polymers.

Each of the three separate batches of the three dexamethasone-polymer blends are then fed into a single-piston thermal extruder and three different extruded dexamethasone-polymer filaments are thereby made. The filaments are further processed to obtain individual segments (implants), each segment being about a 1 mg implant containing approximately 0.5 mg of dexamethasone. The three implant segment system consists of one of each of the 1 mg implants for each of the three polymer mixtures which are combined separately with 0.5 mg of dexamethasone). The total dexamethasone concentration in the combined three implants is about 1.5 mg, as of the three implants weighed about 1 mg and each of the three implants contained about 50% by weight dexamethasone. A three implant dexamethasone extended release system is thereby made.

Example 2

Treatment of an Ocular Condition with an Anti-Inflammatory Active Agent Extended Release System An extended release implant system can be used to treat an ocular condition. The implant can contain a steroid, such an anti-inflammatory steroid, such as dexamethazone as the active agent. Alternately or in addition, the active agent can be a non-steroidal anti-inflammatory, such as ketorolac (available from Allergan, Irvine, Calif. as ketorolac tromethamine ophthalmic solution, under the tradename Acular). Thus, for example, a dexamethasone or ketorolac extended release implant system of Example 1 can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known procedures (trocar implantation). The implant(s) can release a therapeutic amount of, for example the dexamethazone or the ketorolac for an extended period of time to thereby treat a symptom of the ocular condition.

Example 3

Preparation and Therapeutic Use of an Anti-Angiogenesis Extended Release Implant(s)

An implant to treat an ocular condition according to the present invention can contain a steroid, such an anti-angiogenesis steroid, such as an anecortave, as the active agent. Thus, a bioerodible implant system for extended delivery of anecortave acetate (an angiostatic steroid) can be made using the method of Example 1, but with use of anecortave acetate as the active agent, instead of dexamethasone. The implant or implants can be loaded with a total of about 15 mg of the anecortave (i.e. 5 mg of anecortave can be loaded into each of the three implants prepared according to the Example 1 method.

The anecortave acetate extended release implant system can be implanted into an ocular region or site (i.e. into the vitreous) of a patient with an ocular condition for a desired therapeutic effect. The ocular condition can be an angiogenic condition or an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known procedures (trocar implantation). The implant(s) can release a therapeutic amount of the anecortave for an extended period of time to thereby treat a symptom of the ocular condition.

Example 4

Preparation and Therapeutic Use of an Anti-VEGF Extended Release Implant(s)

VEGF (Vascular Endothelial Growth Factor) (also known as VEGF-A) is a growth factor, which can stimulate vascular endothelial cell growth, survival, and proliferation. VEGF is believed to play a central role in the development of new blood vessels (angiogenesis) and the survival of immature blood vessels (vascular maintenance). Tumor expression of VEGF can lead to the development and maintenance of a vascular network, which promotes tumor growth and metastasis. Thus, increased VEGF expression correlates with poor prognosis in many tumor types. Inhibition of VEGF can be an anticancer therapy used alone or to complement current therapeutic modalities (e.g., radiation, chemotherapy, targeted biologic therapies).

VEGF is believed to exert its effects by binding to and activating two structurally related membrane receptor tyrosine kinases, VEGF receptor-1 (VEGFR-1 or flt-1) and VEGFR-2 (flk-1 or KDR), which are expressed by endothelial cells within the blood vessel wall. VEGF may also interact with the structurally distinct receptor neuropilin-1. Binding of VEGF to these receptors initiates a signaling cascade, resulting in effects on gene expression and cell survival, proliferation, and migration. VEGF is a member of a family of structurally related proteins (see Table A below). These proteins bind to a family of VEGFRs (VEGF receptors), thereby stimulating various biologic processes. Placental growth factor (PlGF) and VEGF-B bind primarily to VEGFR-1. PlGF modulates angiogenesis and may also play a role in the inflammatory response. VEGF-C and VEGF-D bind primarily to VEGFR-3 and stimulate lymphangiogenesis rather than angiogenesis.

TABLE A

| VEGF Family Members | Receptors | Functions |
|---|---|---|
| VEGF (VEGF-A) | VEGFR-1, VEGFR-2, neuropilin-1 | Angiogenesis Vascular maintenance |
| VEGF-B | VEGFR-1 | Not established |
| VEGF-C | VEGF-R, VEGFR-3 | Lymphangiogenesis |
| VEGF-D | VEGFR-2, VEGFR-3 | Lymphangiogenesis |
| VEGF-E (viral factor) | VEGFR-2 | Angiogenesis |
| PIGF | VEGFR-1, neuropilin-1 | Angiogenesis and inflammation |

An extended release bioerodible implant system can be used to treat an ocular condition mediated by a VEGF. Thus, the implant can contain as active agent a compound with acts to inhibit formation of VEGF or to inhibit the binding of VEGF to its VERFR. The active agent can be, for example, ranibizumab (rhuFab V2) (Genentech, South San Francisco, Calif.) and the implant(s) can be made using the method of Example 1, but with use of ranibizumab as the active agent, instead of dexamethasone. Ranibizumab is an anti-VEGF (vascular endothelial growth factor) product, which may have particular utility for patients with macular degeneration, including the wet form of age-related macular degeneration. The implant or implants can be loaded with a total of about 300-500 µg of the ranibizumab (i.e. about 150 µg of ranibizumab can be loaded into each of the three implants prepared according to the Example 1 method.

The ranibizumab extended release implant system can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known procedures (trocar implantation). The implant(s) can release a therapeutic amount of the ranibizumab for an extended period of time to thereby treat a symptom of the ocular condition.

Pegaptanib is an aptamer that can selectively bind to and neutralize VEGF and may have utility for treatment of, for example, age-related macular degeneration and diabetic macular edema by inhibiting abnormal blood vessel growth and by stabilizing or reverse blood vessel leakage in the back of the eye resulting in improved vision. A bioerodible implant system for extended delivery of pegaptanib sodium (Macugen; Pfizer Inc, New York or Eyetech Pharmaceuticals, New York) can also be made using the method of Example 1 or the method of Example 4, but with use of pegaptanib sodium as the active agent, instead of dexamethasone. The implant or implants can be loaded with a total of about 1 mg to 3 mg of Macugen according to the Example 1 method.

The pegaptanib sodium extended release implant system can be implanted into an ocular region or site (i.e. into the vitreous) of a patient with an ocular condition for a desired therapeutic effect.

An extended release bioerodible intraocular implant for treating an ocular condition, such as an ocular tumor can also be made as set forth in this Example 9, using about 1-3 mg of the VEGF Trap compound available from Regeneron, Tarrytown, N.Y.

Example 5

Preparation and Therapeutic Use of Beta Blocker Extended Release Implant(s)

An extended release implant system to treat an ocular condition can contain a beta-adrenergic receptor antagonist (i.e. a "beta blocker) such as levobunolol, betaxolol, carteolol, timolol hemihydrate and timolol. Timolol maleate is commonly used to treat of open-angle glaucoma. Thus, an extended release bioerodible implant system containing timolol maleate (available from multiple different suppliers under the tradenames Timoptic, Timolol or Loptomit) as the active agent can be made using the method of Example 1, but with use of timolol maleate instead of dexamethasone. Thus, about 50 µg to 150 µg of the timolol maleate can be loaded into each of the three implants prepared according to the Example 1 method.

The timolol extended release implant system can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known procedures (trocar implantation). The implant(s) can release a therapeutic amount of the timolol for an extended period of time to thereby treat a symptom of the ocular condition by, for example, causing an intraocular pressure depression.

Example 6

Preparation and Therapeutic Use of Prostamide Extended Release Implant(s)

An extended release implant system can be used to treat an ocular condition can contain a prostamide. Prostamides are naturally occurring substances biosynthesized from anandamide in a pathway that includes COX2. Bimatoprost (Lumigan) is a synthetic prostamide analog chemically related to prostamide F. Lumigan has been approved by the FDA for the reduction of elevated intraocular pressure (IOP) in patients with open-angle glaucoma or ocular hypertension who are intolerant of or insufficiently responsive to other IOP-lowering medications. Lumigan is believed to lower intraocular pressure by increasing the outflow of aqueous humor.

Thus, an extended release bioerodible implant system containing Lumigan (Allergan, Irvine, Calif.) as the active agent can be made using the method of Example 1, but with use of timolol maleate instead of dexamethasone. Thus, about 100

μg to 300 μg of Lumigan can be loaded into each of the three implants prepared according to the Example 1 method.

The Lumigan extended release implant system can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known procedures (trocar implantation). The implant(s) can release a therapeutic amount of the Lumigan for an extended period of time to thereby treat a symptom of the ocular condition by, for example, causing an intraocular pressure depression.

Example 7

Preparation and Therapeutic Use of an Alpha-2 Extended Release Implant(s)

An extended release implant system can be used to treat an ocular condition wherein the implant contains as the active agent an alpha-2 adrenergic receptor agonist, such as clonidine, apraclonidine, or brimonidine. Thus, an extended release bioerodible implant system containing brimonidine (Allergan, Irvine, Calif., as Alphagan or Alphagan P) as the active agent can be made using the method of Example 1, but with use of Alphagan instead of dexamethasone. Thus, about 50 μg to 100 μg of Alphagan can be loaded into each of the three implants prepared according to the Example 1 method.

The brimonidine extended release implant system can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known procedures (trocar implantation). The implant(s) can release a therapeutic amount of the brimonidine for an extended period of time to thereby treat a symptom of the ocular condition by, for example, causing an intraocular pressure depression.

Example 8

Preparation and Therapeutic Use of a Retinoid Extended Release Implant(s)

An extended release implant system can be used to treat an ocular condition. The implant can contain a retinoid such as an ethyl nicotinate, such as a tazarotene. Thus, an extended release bioerodible implant system containing tazarotene (Allergan, Irvine, Calif.) as the active agent can be made using the method of Example 1, but with use of tazarotene instead of dexamethasone. Thus, about 100 μg to 500 μg of tazarotene can be loaded into each of the three implants prepared according to the Example 1 method.

The tazarotene extended release implant system can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known procedures (trocar implantation). The implant(s) can release a therapeutic amount of the tazarotene for an extended period of time to thereby treat a symptom of the ocular condition by, for example, causing an intraocular pressure depression.

Example 8

Preparation and Therapeutic Use of a Tyrosine Kinase Inhibitor Extended Release Implant(s)

Generally, tyrosine kinase inhibitors are small molecule inhibitors of growth factor signaling. Protein tyrosine kinases (PTKs) comprise a large and diverse class of proteins having enzymatic activity. The PTKs play an important role in the control of cell growth and differentiation. For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates, which have a catalytic domain; and (2) substrates, which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step, which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular). The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS—R, the IGF-1R and the IR—R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes that lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogene 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci 90: 10705-09; Kim, et al, 1993, Nature 362: 841-844), RNA ligands (Jellinek, et al, Biochemistry 33: 10450-56); Takano, et al, 1993, Mol. Bio. Cell 4:358A; Kinsella, et al, 1992, Exp. Cell Res. 199: 56-62; Wright, et al, 1992, J. Cellular Phys. 152: 448-57) and tyrosine kinase inhibitors (PCT Application Nos. WO 94/03427; WO 92/21660; WO 91/15495; WO 94/14808; U.S. Pat. No. 5,330, 992; Mariani, et al, 1994, Proc. Am. Assoc. Cancer Res. 35: 2268).

An extended release implant system can be used to treat an ocular condition wherein the implant contains a tyrosine kinase inhibitor (TKI) such as a TKI set forth in published U.S. patent application 2004 00019098 (available from Allergan, Irvine, Calif.) as the active agent can be made using the method of Example 1, but with use of a TKI instead of dexamethasone. Thus, about 100 μg to 300 μg of a TKI can be loaded into each of the three implants prepared according to the Example 1 method.

The TKI extended release implant system can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known the procedures (trocar implantation). The implant(s) can release a therapeutic amount of the TKI for an extended period of time to thereby treat a symptom of the ocular condition by, for example, causing an intraocular pressure depression.

Example 9

Preparation and Therapeutic Use of an NMDA Antagonist Extended Release Implant(s)

It is believed that overstimulation of the N-methyl-D-aspartate (NMDA) receptor by glutamate is implicated in a variety of disorders. Memantine is an NMDA antagonist that can be used to reduce neuronal damage mediated by the NMDA receptor complex. Memantine is an available form Merz Pharmaceuticals, Greensboro, N.C. under the tradename Axura. An extended release implant system can be used to treat an ocular condition. The implant can contain an NMDA antagonist such as memantine. Thus, an extended release bioerodible implant system containing memantine as the active agent can be made using the method of Example 1, but with use of memantine instead of dexamethasone. Thus, about 400 μg to 700 μg of memantine can be loaded into each of the three implants prepared according to the Example 1 method.

The memantine extended release implant system can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known procedures (trocar implantation). The implant(s) can release a therapeutic amount of the memantine for an extended period of time to thereby treat a symptom of the ocular condition.

Example 10

Preparation and Therapeutic Use of an Estratropone Extended Release Implant(s)

Certain estratropones have anti-angiogenesis, anti-neoplastic and related useful therapeutic activities. An extended release implant system can be used to treat an ocular condition. The implant can contain an estratropone such as 2-methoxyestradiol (available form Entremed, Inc., of Rockville, Md. under the tradename Panzem). Thus, an extended release bioerodible implant system containing memantine as the active agent can be made using the method of Example 1, but with use of 2-methoxyestradiol instead of dexamethasone. 2-methoxyestradiol can be used as a small molecule angiogenic inhibitor to block abnormal blood vessel formation in the back of the eye. Thus, about 400 μg to 700 μg of 2-methoxyestradiol can be loaded into each of the three implants prepared according to the Example 1 method.

The 2-methoxyestradiol extended release implant system can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using known procedures (trocar implantation). The implant(s) can release a therapeutic amount of the 2-methoxyestradiol for an extended period of time to thereby treat a symptom of the ocular condition.

Using the same methodology, additional extended release single or multiple polymer implants can be prepared wherein the active agent is, for example, an agent to treat intravitreal hemorrhage (such as Vitrase, available from Ista Pharmaceuticals), an antibiotic (such as cyclosporine, or gatifloxacin, the former being available from Allergan, Irvine, Calif. under the tradename Restasis and the later from Allergan under the tradename Zymar), ofloxacin, an androgen, epinastine (Elestat, Allergan, Irvine, Calif.), an anti-coagulant, a metalloprotease inhibitor, a carbonic anhydrase inhibitor, a GABA receptor agonist, a calcium channel antagonist, or with a combination of two or more active agents (such as a combination in a single extended release implant of a prostamide (i.e. brimatoprost) and a best blocker (i.e. timolol) or a combination of an alpha 2 adrenergic agonist (i.e. brimonidine) and a beta blocker, such as timolol) in the same extended delivery system. An implant within the scope of the present invention can be used in conjunction with a photodynamic therapy or laser procedure upon an eye tissue.

All references, articles, patents, applications and publications set forth above are incorporated herein by reference in their entireties.

Accordingly, the spirit and scope of the following claims should not be limited to the descriptions of the preferred embodiments set forth above.

We claim:

1. A method of manufacturing a drug delivery system which comprises a segmented bioerodible implant, the method comprising:
 a) blending a first active agent with a first bioerodible polymer to form a first active agent polymer mixture;
 b) forming the first active agent polymer mixture into a rod shaped first implant segment having a longitudinal axis;
 c) blending a second active agent with a second bioerodible polymer to form a second active agent polymer mixture;
 d) forming the second active agent polymer mixture into a rod shaped second implant segment having a longitudinal axis;
 e) joining the segments at the ends thereof to permit separation from each other in situ into individual segments following implantation into a patient;
 wherein each of the segments is formed with at least one end having a cut surface that is at an angle to the longitudinal axis of less than 90° or one end having a beveled shaped surface; wherein at least one of the segments is formed by a double extrusion process; and wherein the segments erode at different rates in situ.

2. The method according to 1, wherein the first and second bioerodible polymer comprises at least one member selected from the group consisting of poly(lactide) polymers and poly (lactide-co-glycolide) copolymers.

3. The method according to claim 1, wherein at least one excipient that modifies the erosion characteristics of the bioerodible polymer is blended with the active agent and the bioerodible polymer, and wherein the first and second active agent polymer mixtures comprise different excipients.

4. The method according to claim 3, wherein the at least one excipient is a member selected from the group consisting of long chain fatty alcohols, cholesterol, and high molecular weight polyethylene glycol polymers.

5. The method according to claim 1, wherein the first and/or second bioerodible polymer comprises a poly(D,L-lactide-co-glycolide) copolymer with a monomer ratio in the range of 50:50 to 85:15.

* * * * *

UNITED STATES PATENT AND TRADEMARK OFFICE
CERTIFICATE OF CORRECTION

PATENT NO. : 8,231,892 B2
APPLICATION NO. : 11/753419
DATED : July 31, 2012
INVENTOR(S) : Robert T. Lyons et al.

It is certified that error appears in the above-identified patent and that said Letters Patent is hereby corrected as shown below:

On the Title page, Item (56), under "Other Publications", in column 2, line 7, delete "Oncogen" and insert -- Oncogene --, therefor.

In column 1, line 17, delete "aliment"" and insert -- ailment --, therefor.

In column 3, line 3, delete "uveitis"" and insert -- uveitis, --, therefor.

In column 6, line 57, delete "aliment"" and insert -- ailment --, therefor.

In column 11, line 19, delete "oxycillin," and insert -- oxacillin, --, therefor.

In column 11, line 20, delete "polymixin" and insert -- polymyxin --, therefor.

In column 11, line 22, delete "ciproflaxin," and insert -- ciprofloxacin, --, therefor.

In column 11, line 24, delete "gancyclovir," and insert -- ganciclovir, --, therefor.

In column 11, line 26, delete "ciproflaxin," and insert -- ciprofloxacin, --, therefor.

In column 11, line 27, delete "gancyclovir," and insert -- ganciclovir, --, therefor.

In column 11, line 32, delete "⊕-adrenergic" and insert -- β-adrenergic --, therefor.

In column 11, line 37, delete "antiamebic" and insert -- antiamoebic --, therefor.

In column 11, line 42, delete "mebefunolol;" and insert -- levobunolol; --, therefor.

In column 17, line 8, delete "opthalmia," and insert -- ophthalmia, --, therefor.

Signed and Sealed this
Fifth Day of February, 2013

Teresa Stanek Rea
*Acting Director of the United States Patent and Trademark Office*

CERTIFICATE OF CORRECTION (continued)
U.S. Pat. No. 8,231,892 B2

In column 21, line 26, delete "dexamethazone" and insert -- dexamethasone --, therefor.

In column 21, line 52, delete "dexamethazone" and insert -- dexamethasone --, therefor.

In column 23, line 18, delete "VERFR." and insert -- VEGFR. --, therefor.

In column 30, line 14, delete "brimatoprost)" and insert -- bimatoprost) --, therefor.

In column 30, line 48, in Claim 2, delete "1," and insert -- claim 1, --, therefor.